United States Patent [19]

Carini et al.

[11] Patent Number: 4,916,129
[45] Date of Patent: Apr. 10, 1990

[54] COMBINATION β-BLOCKING/ANGIOTENSIN II BLOCKING ANTIHYPERTENSIVES

[75] Inventors: David J. Carini, Wilmington; John J. V. Duncia, Newark, both of Del.

[73] Assignee: E. I. Du Pont de Nemours and Company, Wilmington, Del.

[21] Appl. No.: 299,709

[22] Filed: Jan. 19, 1989

[51] Int. Cl.$^4$ .................. C07D 413/14; C07F 9/65; A61K 31/535
[52] U.S. Cl. .................. 514/235.2; 514/235.8; 514/236.2; 514/381; 514/383; 514/397; 514/399; 514/400; 544/112; 544/132; 544/139; 548/112; 548/119; 548/251; 548/252; 548/336; 548/337; 548/339; 548/341; 548/342; 548/266.2
[58] Field of Search .......... 544/112, 132, 139; 548/112, 119, 251, 252, 255, 262, 269, 336, 337, 339, 341, 342; 514/235.2, 235.8, 236.2, 381, 383, 397, 399, 400

[56] References Cited

U.S. PATENT DOCUMENTS 3,705,907 12/1972 Troxler ............... 269/326.14 R
4,207,324 6/1980 Matsumura et al. ....... 424/273 R
4,340,598 7/1982 Furukawa et al. ........ 424/273 R
4,355,040 10/1982 Furukawa et al. ........ 424/273 R

FOREIGN PATENT DOCUMENTS 0174162 7/1979 European Pat. Off.
0125033 1/1980 European Pat. Off.
0103647 2/1982 European Pat. Off.

Primary Examiner—Mary C. Lee
Assistant Examiner—Richard A. Sharpe

[57] ABSTRACT

Imidazole compounds such as

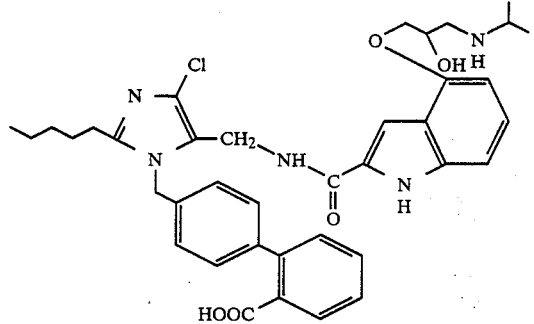

which have angiotensin II antagonizing properties as well as β-adrenoceptor antagonizing properties are useful as antihypertensives and for treatment of congestive heart failure.

5 Claims, 2 Drawing Sheets

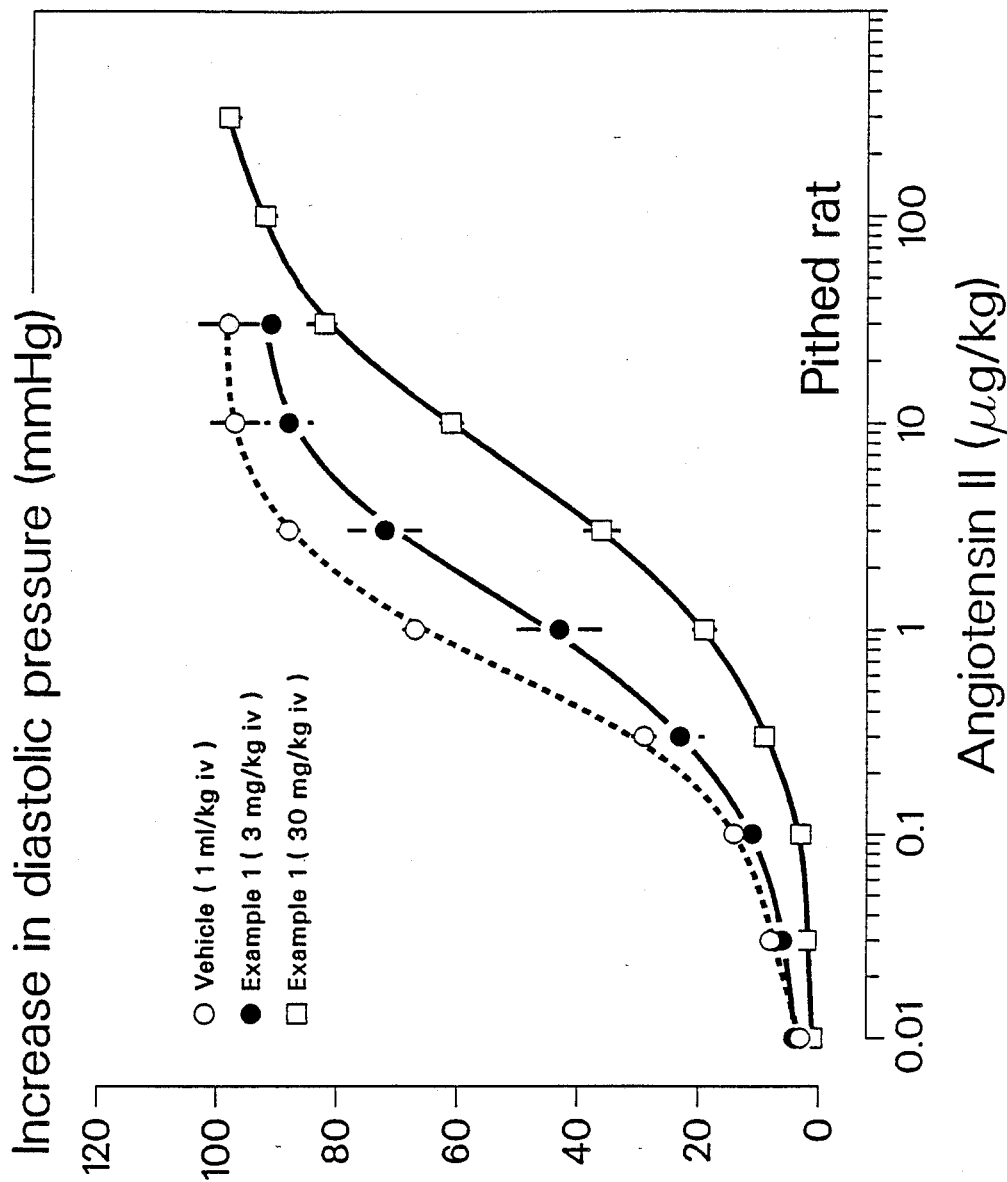

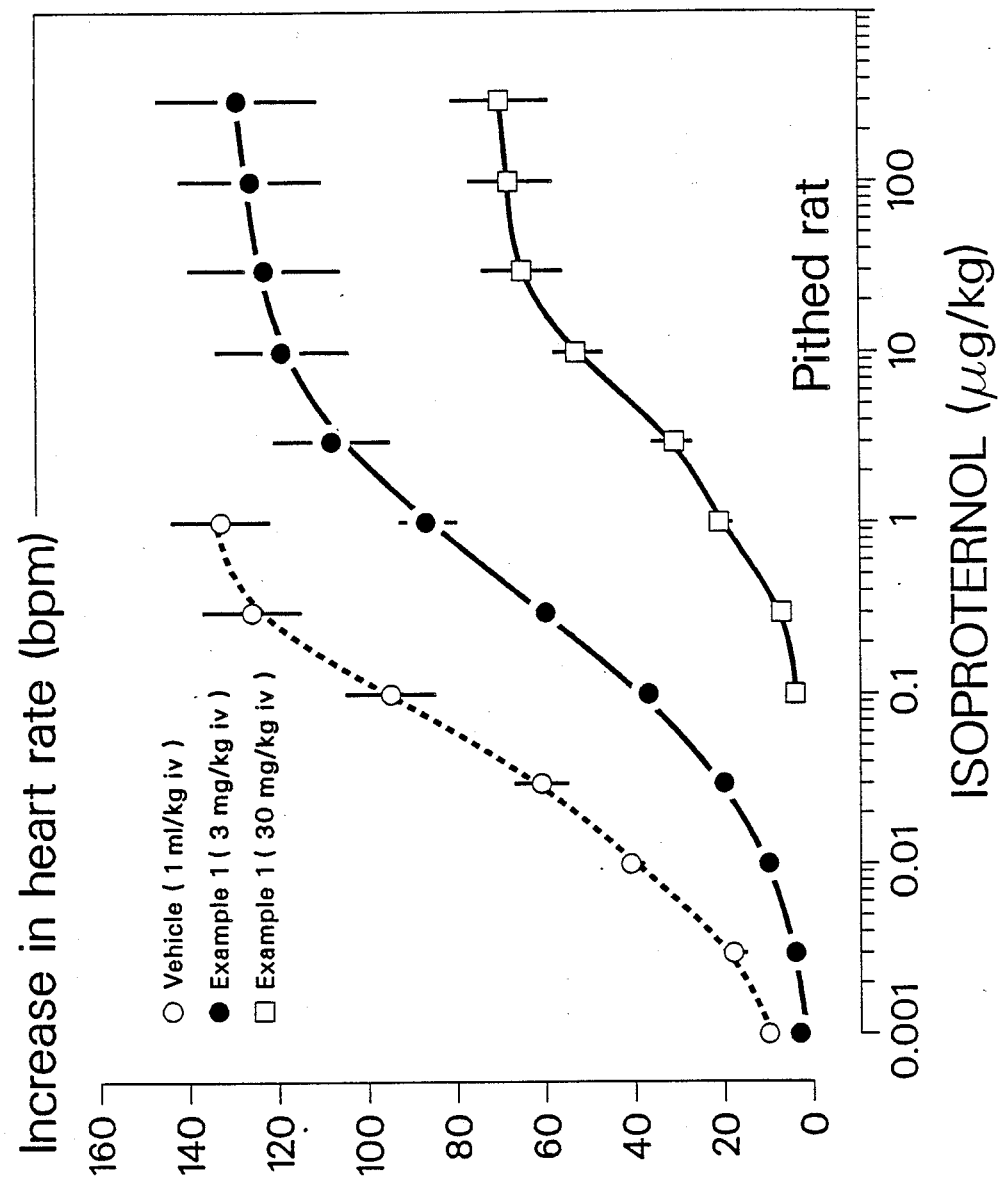

COMBINATION β-BLOCKING/ANGIOTENSIN II BLOCKING ANTIHYPERTENSIVES

BACKGROUND OF THE INVENTION

This invention relates to novel imidazole compounds, processes for preparing them, pharmaceutical compositions containing them, and their use to treat hypertension and congestive heart failure.

U.S. Pat. Nos. 4,207,324, 4,355,040 and 4,340,598 and European patent application Publication No. 103,647 disclose antihypertensive imidazole compounds. In our commonly-assigned U.S. application Ser. Nos. 884,920, 07/050,341, 07/142,580 and 07/279,194 and European patent application Publication No. 0253310 (published Jan. 20, 1988) we have disclosed imidazole compounds which inhibit the action of the hormone angiotensin II (AII) and are useful therefore in alleviating angiotensin induced hypertension and are also useful in the treatment of congestive heart failure.

U.S. Pat. No. 3,705,907 discloses amino(hydroxy)alkoxy aryl compounds which block the β-adrenergic receptor and are useful in treatment of hypertension. European patent application Publication No. 0174162 discloses antihypertensive amino(hydroxy)alkoxy aryl compounds which not only block the β-receptor but also inhibit the angiotensin converting enzyme which converts angiotensin I to AII.

There are no compounds known to date which combine the properties of β-adrenergic receptor blocking and AII receptor blocking.

SUMMARY OF THE INVENTION

According to the present invention, there are provided novel compounds of Formula (I) which have angiotensin II antagonizing as well as β-adrenoreceptor antagonizing properties, which makes them useful as antihypertensives.

$$\text{(I)}$$

wherein
Q and $Q^1$–$Q^6$ are independently selected from hydrogen and alkyl of 1–4 carbon atoms;
P is a carbonyl group or $$-\overset{O}{\underset{\|}{C}}-NH- \quad \text{or} \quad -\overset{O}{\underset{\|}{C}}-O-$$

with N and O, respectively, bonded to AR;
B is an alkyl group of 1 to 6 carbon atoms;
Any of the $-(CH_2)_c-$ groups independently are optionally substituted by one or two alkyl groups of 1 to 4 carbon atoms;
Ar is a benzene ring or a naphthyl or indolyl ring system any of which is optionally substituted in any position by one or more substituents independently selected from alkyl groups of 1 to 4 carbon atoms being optionally substituted by one or more halogen atoms, alkoxy of 1 to 9 carbon atoms, halogen, nitro, amino, carboxy, alkoxycarbonyl of 1 to 4 carbon atoms, and hydroxy;
$R^1$ is $-4-COOH$; $-4-CO_2R^7$;

$$\text{structures shown}$$

$NHSO_2CF_3$; $CONHOR^9$.

$R^2$ is H, F, Cl, Br, I, $NO_2$, alkyl of one to six carbon atoms, perfluoroalkyl of one to six carbon atoms, phenyl, pentafluorophenyl, CN, $COR^{16}$;
$R^3$ is alkyl of 2 to 10 carbon atoms, alkenyl or alkynyl of 3 to 10 carbon atoms, alkylthio of 2–10 carbon atoms;
$R^4$ is H; Cl; Br; F; $NO_2$; alkyl of 1 to 4 carbon atoms; acyloxy of 1 to 4 carbon atoms; alkoxy of 1 to 4 carbon atoms; $CO_2H$; $CO_2R^7$; $NHSO_2CH_3$; $NHSO_2CF_3$; $CONHOR^9$; $SO_2NH_2$; aryl or furyl;
$R^5$ is H; Cl, Br, I or F; alkyl of 1 to 4 carbon atoms or alkoxy of 1 to 4 carbon atoms;
$R^6$ is $-CO_2H$; $-CO_2R^7$; $-CH_2CO_2H$, $-CH_2CO_2R^7$;

$$-O-\overset{O}{\underset{\underset{OH}{|}}{\overset{\|}{S}}}-OH; \quad -O-\overset{O}{\underset{\underset{OH}{|}}{\overset{\|}{P}}}-OH; \quad -SO_3H; \quad -NH\overset{O}{\underset{\underset{OH}{|}}{\overset{\|}{P}}}-OH;$$

$-PO_3H$; $-C(CF_3)_2OH$; $-NHSO_2CH_3$; $-NHSO_2CF_3$;

$-NHCOCF_3$; $-CONHOR^9$; $-SO_2NH_2$; $-CH_2-$ tetrazole;

$-CONH-$ tetrazole; $CONHNHSO_2CF_3$; tetrazole-$CF_3$;

other heterocycles shown;

$R^7$ is $$-\overset{R^{14}}{\underset{|}{CH}}-O\overset{O}{\underset{\|}{C}}R^{11};$$

$R^8$ is H, alkyl of 1 to 6 carbon atoms, cycloalkyl of 3 to 6 carbon atoms, phenyl or benzyl;
$R^9$ is H, methyl or benzyl;
$R^{11}$ is alkyl of 1 to 6 carbon atoms; $-NR^{12}R^{13}$; or $$-\underset{\underset{NH_2}{|}}{CH}CH_2CO_2CH_3$$

$R^{12}$ and $R^{13}$ are independently H, alkyl of 1 to 6 carbon atoms, benzyl, or are taken together as $(CH_2)_u$ where u is 3 to 6;

$R^{14}$ is H, $CH_3$ or $-C_6H_5$;

$R^{15} = CN$, $NO_2$ or $CO_2R^8$;

$R^{16}$ is H; alkyl of 1 to 6 carbon atoms; phenyl; phenylalkyl where alkyl is 1 to 6 carbon atoms; OH; alkoxy of 1 to 6 carbon atoms; phenoxy; benzyloxy; $NH_2$; alkylamino or dialkylamino where alkyl is 1 to 6 carbon atoms; or morpholino;

X is a carbon-carbon single bond, $-CO-$, $-O-$, $-S-$, $-NH-$, $-NHCO-$, $-CONH-$, $-OCH_2$, $-CH_2O-$, $-CH=CH-$, $-SCH_2-$, $-NHCH_2-$, $-CH_2-$, $-CH_2S-$, $-CH_2NH-$;

Z = O, S;

c = 1 to 10;

r = 0 to 2;

and pharmaceutically acceptable salts of these compounds.

When Ar represents a benzene ring, the P group can be attached at the ortho, meta or para position relative to the amino(hydroxy) alkoxy moiety. When Ar represents an indolyl ring system, most preferably the amino(hydroxy) alkoxy moiety is attached in the 4 or 5 position and the P group is in the 2 or 3 position. When Ar represents a naphthalene ring system, the amino(hydroxy) alkoxy moiety is preferably in the 1 or 2 position and the P group is in the 6 or 7 position.

Within the scope of this invention are pharmaceutical compositions comprising a suitable pharmaceutical carrier and a compound of Formula (I), and methods of using the compounds of Formula (I) to treat hypertension and congestive heart failure. The compounds of this invention can also be used as diagnostic agents to test the renin angiotensin system.

Synthesis

The novel compounds of Formula (I) may be prepared using the reactions and techniques described in this section. The reactions are performed in a solvent appropriate to the reagents and materials employed and suitable for the transformation being effected. It is understood by those skilled in the art of organic synthesis that the functionality present on the imidazole and other portions of the molecule must be consistent with the chemical transformations proposed. This will frequently necessitate judgment as to the order of synthetic steps, protecting groups required, deprotection conditions, and activation of a benzylic position to enable attachment to nitrogen on the imidazole nucleus. Throughout the following section, not all compounds of Formula (I) falling into a given class may necessarily be prepared by all methods described for that class. Substituents on the starting materials may be incompatible with some of the reaction conditions required in some of the methods described. Such restrictions to the substituents which are compatible with the reaction conditions will be readily apparent to one skilled in the art and alternative methods described must then be used.

The compounds of Formula (I) and their physiologically acceptable salts may be prepared in any conventional manner and in accordance with the present invention may, for example, be prepared by any method hereinafter described. In particular, the compounds of Formula (I) and their physiologically acceptable salts may be prepared by any of the methods standard in the art of peptide chemistry and may comprise coupling the aryl moiety, the amino(hydroxy)alkoxy side chain and the aminoalkylimidazole derivative which together form the compounds of Formula (I), in any desired order. It will be appreciated that, for example, the aryl moiety, the amino(hydroxy)alkoxy side chain, and the aminoalkylimidazole portion or their derivatives may be coupled in any order to form two separate chemical entities which, as a final process stage (which we may claim as an aspect of the present invention), are then coupled to form the compound of Formula (I) or a precursor thereof and, if appropriate, converting the precursor (which conversion we may also claim as an aspect of the present invention) to the desired compound of Formula (I), and optionally, if desired, converting the compound of Formula (I) to another compound of Formula (I), and also optionally, if desired, converting any compound of Formula (I) so formed to a phsiologically acceptable salt thereof.

According to the present invention, we also provide a process for the preparation of a compound of Formula (I) or a physiologically acceptable salt thereof which comprises coupling compound 1 with a compound 2 where both 1 and 2 are in suitably

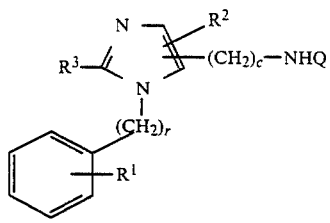

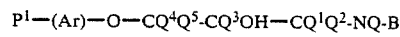

protected forms to yield (I) in a protected form. Subsequent deprotection yields the product of Formula (I). $p^1$ can be $-COOH$; an activated derivative of $-COOH$ such as $-COCl$ or $-CO-$active ester; an isocyanate ($O=C=N-$); and an activated carbamate precursor $L-CO-O-$ where L is an activated leaving group such as Cl, or N-imidazole.

The synthesis of 1 is described in detail in EP 0253310-A2, which is incorporated herein by reference, particularly pages 18-33; page 34, lines 1-9; pages 40-41; page 42, lines 1-23; pages 44-46; pages 49-50; page 51, lines 1-18 and lines 26-35; pages 52-58; page 59, lines 1-13; pages 60-61; page 62, lines 20-27; page 63, lines 12-15 and lines 27-29; pages 64-66; page 67, lines 1-12; page 69, lines 28-29; pages 70-72; page 74, lines 15-30; pages 84-91; page 94, lines 5-12 and lines 21-34; page 95, lines 1-4 and Scheme 33; page 96, lines 4-15; page 97, Scheme 34, transformation 25 to 222; page 98, lines 13-35.

When $p^1$ is COOH, then 1 and 2 may be coupled by a variety of known peptide coupling procedures to yield Formula (I). For example, 1,3-dicyclohexyl carbodiimide facilitated coupling, diphenylphosphoryl azide facilitated coupling, and the mixed anhydride coupling procedures carried out in non-hydroxylic solvents such as THF, DMF, methylene chloride at 0° to room temperature are well known to those skilled in the art of making amide or peptide bonds.

The COOH group of 2 can also be converted into an activated from such as an acid chloride or active ester which can be isolated ($p^1 = COCl$ or $CO-$ active ester) and reacted with 1. N-hydroxysuccinimide or p-nitrophenyl esters are just two examples of activated esters which can be used in this amide bond formation. These active esters are coupled with 1 in non-hydroxylic solvents at 0° C. to room temperature. In the case of p¹=COCl, the coupling is performed in the presence of an acid scavenger such as potassium carbonate, sodium bicarbonate, or pyridine.

Details of the methods of peptide chemistry and, in particular, suitable activating and protecting groups and of suitable reaction conditions for the above processes may be found in the following literature which is given purely by way of exemplification and which is intended to be neither exhaustive nor limiting:

(1) "The Peptides: Analysis, Synthesis, Biology", Gross, E. and Meienhofer, J. eds., Vols. 1 to 4 (Academic Press, 1979).

(2) "Principles of Peptide Synthesis", Bodanszky, M. (Springer-Verlag, 1984).

When p¹ of 2 is O=C=N— or an activated carbamate precursor such as Cl—CO—O or N—imidazolyl—CO—O— (generated in situ), then reaction of 2 with 1 to yield (I) can be done by simply stirring the two in an inert non-hydroxylic solvent such as described previously at 0° to room temperature. When p¹=Cl—CO—O—, an acid scavenger is also required as described previously for the case when p¹=COCl.

Suitably protected forms of 2 are those where the nitrogen on the isopropanol side chain is protected by the typical N-protecting groups known to one skilled in the art of protecting amino acids. Thus, BOC, CBZ, FMOC, are only a few examples of these N-protecting groups as discussed in "Protective Groups in Organic Synthesis", Greene, T. W. (John Wiley, 1981) pp. 219 ff.

Meanwhile, the hydroxyl group can be free or protected by a wide variety of alcohol protecting groups, such as TMS, TBDMS, benzyl, trityl, THP, etc., as found in "Protective Groups in Organic Synthesis", Greene, T. W. (John Wiley & Sons, 1981) pp. 10 ff. The amino and hydroxyl groups can both be protected by one protecting group, for example, as in a heterocycle. One such example is a cyclic aminal with benzaldehyde which can later be deprotected by aqueous acid.

The synthesis of 2 can be found, for example, for Ar=indole in U.S. Pat. No. 3,705,907. The same type of reaction sequence may be used for the case when Ar= benzene or naphthalene starting from the appropriately protected phenol or naphthol derivative reflecting the synthetic scheme used with hydroxyindole in U.S. Pat. No. 3,705,907.

p¹=—N=C=O may be obtained from either the corresponding —NH₂ or through a Curtius rearrangement [J. Pfister, W. E. Wymann, Synthesis (1983) 38] performed on the corresponding carboxylic acid (p¹=COOH). Amines when reacted with phosgene or its equivalents such as trichloromethyl chloroformate (K. Kurita et al., J. Org. Chem. 41, 2070 (1976); K. Kurita et al., Org. Synth. 59, 195 (1980); S. Ozaki et al., Bull. Chem. Soc. Japan 50, 2406 (1977) yield isocyanates.

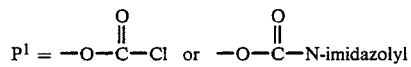

may be obtained through the reaction of the corresponding Ar—OH derivative with excess phosgene, its equivalents such as trichloromethyl chloroformate (T. Matsui, et al., Jpn. Pat. No. 795,942; Chem. Abstr. 91 56666) or carbonyldiimidazole.

Compounds of Formula (I) may also be made by coupling compounds 3 and 4 followed by appropriate elaboration and/or deprotection.

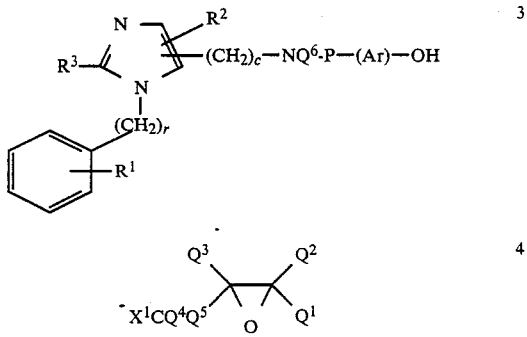

When $X^1$=Cl (for example, epichlorohydrin) or another leaving group, then the oxygen anion of 3 is reacted with 4 to generate an intermediate epoxyether which in situ is opened up with an amine to the corresponding amino-alcohol which after deprotection yields (I). These sequential nucleophilic displacements are carried out in non-hydroxylic solvents such as THF, DMF, and dioxane, or in aqueous/organic mixtures. The oxygen anion may be generated with aqueous NaOH or sodium hydride.

Epoxide 4a, where $p^2$ is a protecting group such as BOC, can be reacted with the oxygen anion of 3 to yield 5. Compound 5 is then N-deprotected and either alkylated with an alkylhalide, tosylate or mesylate, or reductively aminated with an aldehyde or ketone to put on the appropriate B group in (I). Final deprotection, if necessary, yields (I).

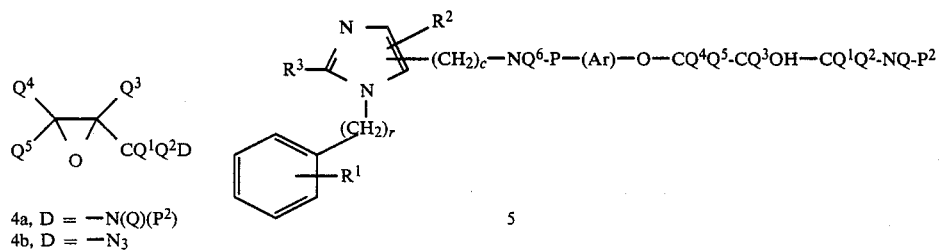

4a, D = —N(Q)(P²)
4b, D = —N₃

Q—N—p² in compound 4a can also be replaced by N₃ as in 4b. The synthesis of 5 would then follow the same reaction sequence as for 4a, except that after O-alkylation, the azide group must first be reduced to the amine by catalytic hydrogenation or homogeneously by methods familiar to one skilled in the art. Then if Q≠H in (I), Q may be introduced by alkylation of the corresponding alkylhalide, tosylate or mesylate. B (B≠H) can also be introduced in a similar fashion to yield (I). Q and B can also be independently introduced, if necessary, by reductively aminating the corresponding aldehyde or ketone onto the free amino group.

Compound 4 can also be optically active for example the oxygen anion of 3 in DMF will yield epoxyether 6 which after fluoride anion induced desilylation (with n-Bu$_4$NF, for example) and epoxide ring opening with an amine will yield (Ia) as one enantiomer:

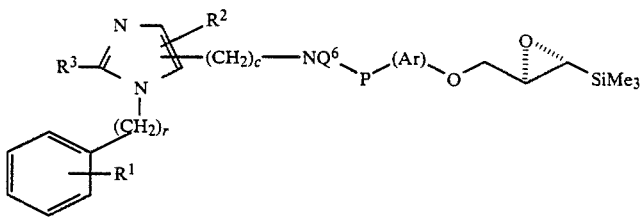

6

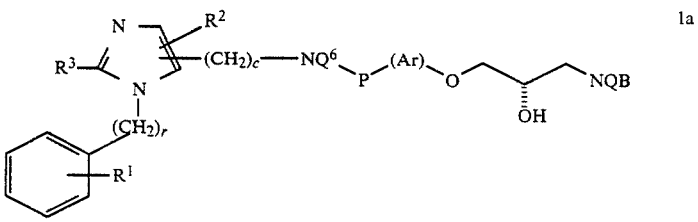

Ia compound 4c, where $Q_1$=Me$_3$Si, $Q_2$—$Q_5$=H and $X^1$=O—Ms where Ms is a mesylate, used in an asymmetric synthesis of (−)-propranalol (T. Katsuki, Tet. Lett. (1984) 25, 2821). Thus, reaction of 4c with

4c

Compound 4 can also be a racemic or optically active glycidol derivative (4d, glycidol: $Q^1$—$Q^5$=H; $X^1$=OH). Two asymmetric syntheses of (Ia) using optically active glycidol (J. M. Klunder, S. Y. Ko, K. B. Sharpless J. Org. Chem. (1986) 51, 3710) are shown below using the oxygen anion of 3 (Schemes 1 and 2).

Scheme 1

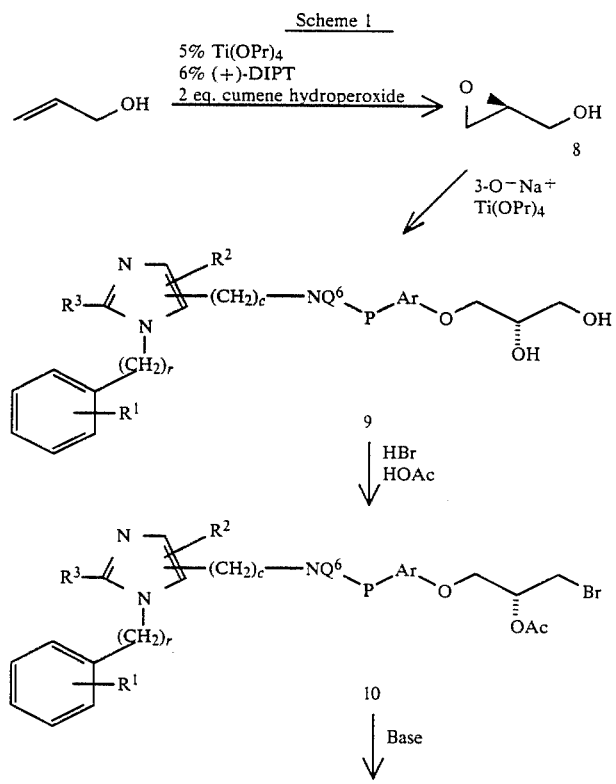

Scheme 1
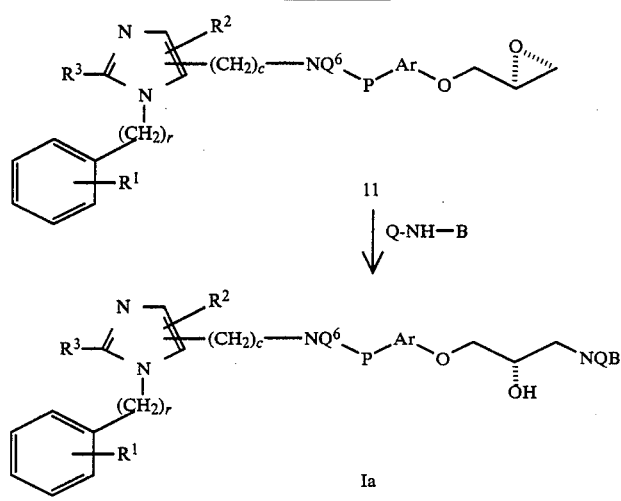
Scheme 2
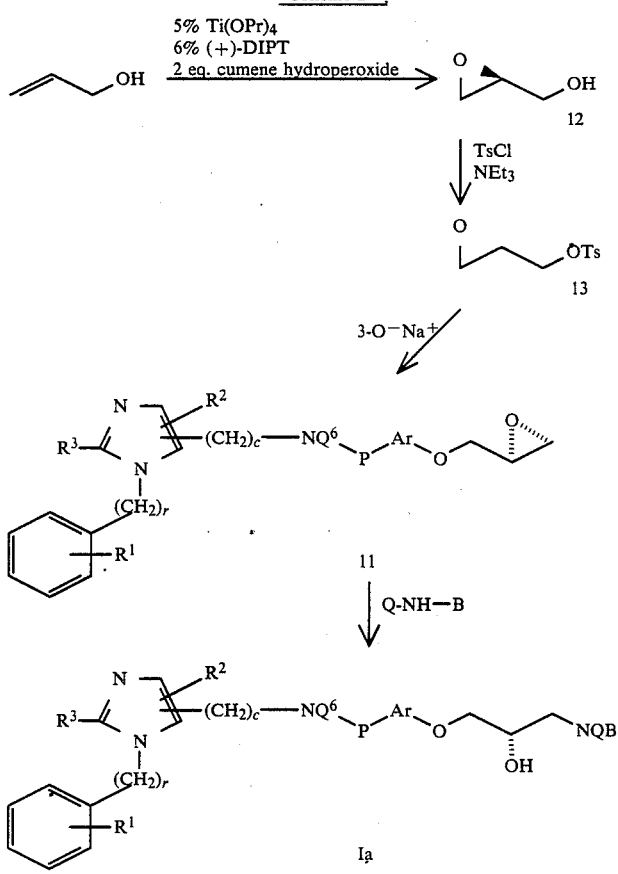
Cardillo, et. al. (G. Carolillo, M. Orena, S. Sandi, *J. Org. Chem.* (1986) 51, 713) has synthesized oxazolidinone 14 which can in the usual fashion be coupled with the oxygen anion of 3 followed by base hydrolysis to yield (Ia). The isopropyl group in 14 may be replaced by the more general structure 15.
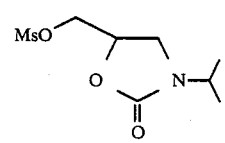

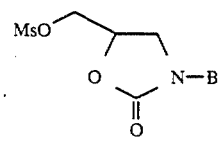

The compounds of this invention and their preparation can be understood further by the following examples, which do not constitute a limitation of the invention.

EXAMPLE 1

Part A: Preparation of 5-[4-(3-(N-t-butoxycarbonyl-N-isopropylamino)-2-hydroxypropoxy)indole-2-carboxamidomethyl]-2-n-butyl-1-[(2'-carbomethoxybiphenyl-4-yl)methyl]-4-chloroimidazole 5-Aminomethyl-2-n-butyl-1-[(2'-carbomethoxybiphenyl-4-yl)methyl]-4-chloroimidazole (prepared by the procedure of Example 148, Part C, in EP No. 0253310) (0.71 g, 1.7 mmol), 1 eq), 4-[3-(N-t-butoxycarbonyl-N-isopropylamino)-2-hydroxypropoxy]indole-2-carboxylic acid (prepared by the procedure of Example 1, Part g, in EPO No. 174162) (0.84 g, 1.7 mmol, 1 eq), 1-hydroxybenzotriazole (0.24 g, 1.8 mmol, 1.05 eq), dicyclohexylcarbodiimide (0.37 g, 1.8 mmol, 1.05 eg) and DMF (25 mL) were mixed at 0° C. and left in the refrigerator for 4 days at that temperature. The dicyclohexylurea was filtered off and the mixture concentrated and chromatographed in 1:1 hexane/ethyl acetate yielding 970 mg of a white solid; mp 157.5°–160° C.

NMR (200MHz,D$_6$DMSO) δ11.51(s,1H); 8.83(M,1H); 7.68(m,1H); 7.44(m,2H); 7.22–6.92(m,8H); 6.43(d,1H, J=7Hz); 5.34(s,2H); 5.05(d1H,J=7Hz); 4.44(m,2H); 3.97(m,4H); 3.49(s,3H); 3.05(m,1H); 2.51(t,2H, J=7Hz); 1.75–1.00(m,4H); 1.35(s,9H); 1.13(d,3H, J=7Hz); 1.08(d,3H,J=7Hz); 0.80(t.3H,J=7Hz).

Anal. Calcd. for $C_{43}H_{52}ClN_5O_7$: c,65.68; H,6.67; Cl,4.51; N,8.91. Found: C,65.47; H,6.93; Cl,4.25; N,8.75.

The compounds below can be made by the method described in Example 1, Part A, and by the cited procedure described in EP No. 0253310-A2:

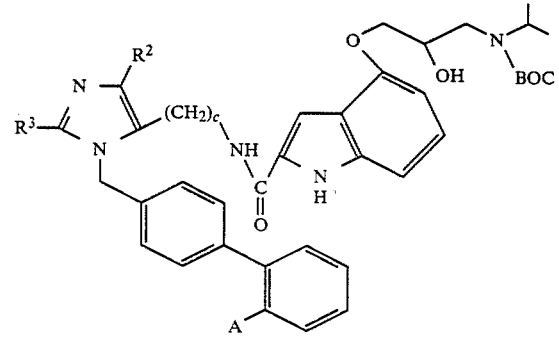

| Example No. | R$^2$ | R$^3$ | n | A | m.p. |
|---|---|---|---|---|---|
| 2 | Cl | n-butyl | 1 | N-(triphenylmethyl)tetrazol-5-yl | |
| 3 | Cl | n-butyl | 2 | N-(triphenylmethyl)tetrazol-5-yl | |
| 4 | Cl | n-butyl | 3 | N-(triphenylmethyl)tetrazol-5-yl | |
| 5 | Cl | n-butyl | 4 | N-(triphenylmethyl)tetrazol-5-yl | |

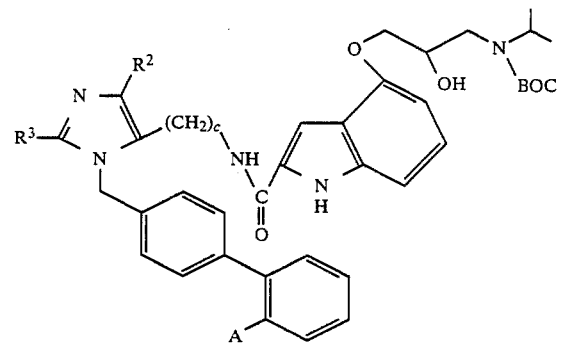

| Example No. | R$^2$ | R$^3$ | n | A | m.p. |
|---|---|---|---|---|---|
| 6 | Cl | n-butyl | 5 | N-(triphenylmethyl)tetrazol-5-yl | |
| 7 | Cl | n-propyl | 1 | N-(triphenylmethyl)tetrazol-5-yl | |
| 8 | Cl | n-propyl | 2 | N-(triphenylmethyl)tetrazol-5-yl | |
| 9 | Cl | n-propyl | 3 | N-(triphenylmethyl)tetrazol-5-yl | |
| 10 | Cl | n-propyl | 4 | N-(triphenylmethyl)tetrazol-5-yl | |
| 11 | Cl | n-propyl | 5 | N-(triphenylmethyl)tetrazol-5-yl | |
| 12 | Cl | n-propyl | 1 | COOMe | |
| 13 | Cl | n-propyl | 2 | COOMe | |
| 14 | Cl | n-propyl | 3 | COOMe | |
| 15 | Cl | n-propyl | 4 | COOMe | |
| 16 | Cl | n-propyl | 5 | COOMe | |
| 17 | Cl | n-butyl | 1 | COOMe | |
| 18 | Cl | n-butyl | 2 | COOMe | |
| 19 | Cl | n-butyl | 3 | COOMe | |
| 20 | Cl | n-butyl | 4 | COOMe | |
| 21 | Cl | n-butyl | 5 | COOMe | |
| 22 | CF$_3$ | n-butyl | 1 | N-(triphenylmethyl)tetrazol-5-yl | |
| 23 | Br | n-butyl | 1 | N-(triphenylmethyl)tetrazol-5-yl | |
| 24 | I | n-butyl | 2 | N-(triphenylmethyl)tetrazol-5-yl | |
| 25 | F | n-butyl | 2 | N-(triphenylmethyl)tetrazol-5-yl | |
| 26 | NO$_2$ | n-butyl | 3 | N-(triphenylmethyl)tetrazol-5-yl | |
| 27 | CF$_3$ | n-butyl | 4 | N-(triphenylmethyl)tetrazol-5-yl | |
| 28 | Br | n-butyl | 4 | N-(triphenylmethyl)tetrazol-5-yl | |
| 29 | F | n-butyl | 5 | N-(triphenylmethyl)tetrazol-5-yl | |
| 30 | NO$_2$ | n-butyl | 5 | N-(triphenylmethyl)tetrazol-5-yl | |
| 31 | CF$_3$ | n-propyl | 1 | N-(triphenylmethyl)tetrazol-5-yl | |
| 32 | Br | n-propyl | 1 | N-(triphenylmethyl)tetrazol-5-yl | |
| 33 | I | n-propyl | 2 | N-(triphenylmethyl)tetrazol-5-yl | |
| 34 | F | n-propyl | 2 | N-(triphenylmethyl)tetrazol-5-yl | |
| 35 | NO$_2$ | n-propyl | 3 | N-(triphenylmethyl)tetrazol-5-yl | |
| 36 | CF$_3$ | n-propyl | 3 | N-(triphenylmethyl)tetrazol-5-yl | |
| 37 | Br | n-propyl | 4 | N-(triphenylmethyl)tetrazol-5-yl | |
| 38 | F | n-propyl | 4 | N-(triphenylmethyl)tetrazol-5-yl | |
| 39 | NO$_2$ | n-propyl | 5 | N-(triphenylmethyl)tetrazol-5-yl | |
| 40 | CF$_3$ | n-propyl | 5 | N-(triphenylmethyl)tetrazol-5-yl | |
| 41 | CF$_3$ | n-butyl | 1 | COOMe | |
| 42 | Br | n-butyl | 1 | COOMe | |
| 43 | I | n-butyl | 2 | COOMe | |
| 44 | F | n-butyl | 2 | COOMe | |
| 45 | NO$_2$ | n-butyl | 3 | COOMe | |
| 46 | CF$_3$ | n-butyl | 4 | COOMe | |
| 47 | Br | n-butyl | 4 | COOMe | |
| 48 | F | n-butyl | 5 | COOMe | |
| 49 | NO$_2$ | n-butyl | 5 | COOMe | |
| 50 | CF$_3$ | n-propyl | 1 | COOMe | |
| 51 | Br | n-propyl | 1 | COOMe | |
| 52 | I | n-propyl | 2 | COOMe | |
| 53 | F | n-propyl | 2 | COOMe | |
| 54 | NO$_2$ | n-propyl | 3 | COOMe | |
| 55 | CF$_3$ | n-propyl | 4 | COOMe | |
| 56 | Br | n-propyl | 4 | COOMe | |
| 57 | F | n-propyl | 5 | COOMe | |
| 58 | NO$_2$ | n-propyl | 5 | COOMe | |

Part B: Preparation of 5-[4-(3-(N-isopropylamino)-2-hydroxypropoxy)indole-2-carboxamidomethyl]-2-n-butyl-1-[(2'-carbomethoxybiphenyl-4-yl)methyl]-4-chloroimidazole To a solution of the compound from Part A (1.51 g) in THF (7.5 mL) was added anisole (7.5 mL), water (7.5 mL), and trifluoroacetic acid (7.5 mL). The above were mixed and stirred at 25° C. for 7 hours. Afterwards, ether was added to triturate gum. The mother liquor was decanted and the hygroscopic gum pumped under high vacuum overnight, yielding 1.68 g of a hard glass.

NMR (D$_6$DMSO) δ11.58(s,1H), 8.80(m,1H); 8.43(m,2H); 7.70(d,1H,J=9Hz); 7.48(m,2H); 7.23–6.97(m,8H); 6.52(d,1H,J=9Hz); 5.37(s,2H); 4.44(d,2H,J=5Hz); 4.30–4.00(m,4H); 3.50(s,3H); 3.33(m,1H); 3.12(m,2H); 2.53(t,2H,J=7Hz); 1.50(t of t,2H,J=7,7Hz); 1.32–1.15(m,8H); 0.80(t,3H,J=7Hz).

The following compounds can be prepared by the method described in Example 1, Part B:

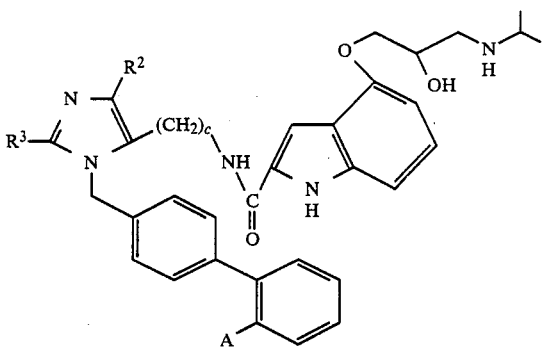

| Example No. | R$^2$ | R$^3$ | n | A | m.p. |
|---|---|---|---|---|---|
| 59 | Cl | n-butyl | I | Tetrazol-5-yl | |
| 60 | Cl | n-butyl | 2 | Tetrazol-5-yl | |
| 61 | Cl | n-butyl | 3 | Tetrazol-5-yl | |
| 62 | Cl | n-butyl | 4 | Tetrazol-5-yl | |
| 63 | Cl | n-butyl | 5 | Tetrazol-5-yl | |
| 64 | Cl | n-propyl | 1 | Tetrazol-5-yl | |
| 65 | Cl | n-propyl | 2 | Tetrazol-5-yl | |
| 66 | Cl | n-propyl | 3 | Tetrazol-5-yl | |
| 67 | Cl | n-propyl | 4 | Tetrazol-5-yl | |
| 68 | Cl | n-propyl | 5 | Tetrazol-5-yl | |
| 69 | CF$_3$ | n-butyl | 1 | Tetrazol-5-yl | |
| 70 | Br | n-butyl | 1 | Tetrazol-5-yl | |
| 71 | I | n-butyl | 2 | Tetrazol-5-yl | |
| 72 | F | n-butyl | 2 | Tetrazol-5-yl | |
| 73 | NO$_2$ | n-butyl | 3 | Tetrazol-5-yl | |
| 74 | CF$_3$ | n-butyl | 4 | Tetrazol-5-yl | |
| 75 | Br | n-butyl | 4 | Tetrazol-5-yl | |
| 76 | F | n-butyl | 5 | Tetrazol-5-yl | |
| 77 | NO$_2$ | n-butyl | 5 | Tetrazol-5-yl | |
| 78 | CF$_3$ | n-propyl | 1 | Tetrazol-5-yl | |
| 79 | Br | n-propyl | 1 | Tetrazol-5-yl | |
| 80 | I | n-propyl | 2 | Tetrazol-5-yl | |
| 81 | F | n-propyl | 2 | Tetrazol-5-yl | |
| 82 | NO$_2$ | n-propyl | 3 | Tetrazol-5-yl | |
| 83 | CF$_3$ | n-propyl | 4 | Tetrazol-5-yl | |
| 84 | Br | n-propyl | 4 | Tetrazol-5-yl | |
| 85 | F | n-propyl | 5 | Tetrazol-5-yl | |
| 86 | NO$_2$ | n-propyl | 5 | Tetrazol-5-yl | |
| Intermediates | | | | | |
| | Cl | n-propyl | 1 | COOMe | |
| | Cl | n-propyl | 2 | COOMe | |
| | Cl | n-propyl | 3 | COOMe | |
| | Cl | n-propyl | 4 | COOMe | |
| | Cl | n-propyl | 5 | COOMe | |
| | Cl | n-butyl | 1 | COOMe | |
| | Cl | n-butyl | 2 | COOMe | |
| | Cl | n-butyl | 3 | COOMe | |
| | Cl | n-butyl | 4 | COOMe | |
| | Cl | n-butyl | 5 | COOMe | |
| | CF$_3$ | n-propyl | 1 | COOMe | |
| | Br | n-propyl | 1 | COOMe | |
| | I | n-propyl | 2 | COOMe | |
| | F | n-propyl | 2 | COOMe | |
| | NO$_2$ | n-propyl | 3 | COOMe | |
| | CF$_3$ | n-propyl | 4 | COOMe | |
| | Br | n-propyl | 4 | COOMe | |
| | F | n-propyl | 5 | COOMe | |
| | NO$_2$ | n-propyl | 5 | COOMe | |
| | CF$_3$ | n-butyl | 1 | COOMe | |
| | Br | n-butyl | 1 | COOMe | |
| | I | n-butyl | 2 | COOMe | |
| | F | n-butyl | 2 | COOMe | |
| | NO$_2$ | n-butyl | 3 | COOMe | |
| | CF$_3$ | n-butyl | 4 | COOMe | |
| | Br | n-butyl | 4 | COOMe | |
| | F | n-butyl | 5 | COOMe | |
| | NO$_2$ | n-butyl | 5 | COOMe | |

Part C: Preparation of 5-[4-(3-(N-isopropylamino)-hydroxypropoxy)indole-2-carboxamidomethyl]-2-n-butyl-1-[(2'-carboxybiphenyl-4-yl)methyl]-4-chloroimidazole The compound from Part B (1.68 g) was mixed and stirred with THF (25 ml), methanol (75 ml), water (5 ml) and 1.000N NaOH (64.0 ml) under N$_2$ at 50° C. for 24 hours. The organic solvents were removed in vacuo when the sodium salt of the product precipitated from the remaining aqueous mixture. The solids were filtered and redissolved in water (50 ml) and ethyl acetate (50 ml) and the pH adjusted to 1 with conc. HCl. The layers were separated and the aqueous layer was extracted with ethyl acetate (2×100 ml). The organic layers were combined, dried (MgSO$_4$) and the solvent removed in vacuo to yield 210 mg of a white solid. The pH of the aqueous layer was readjusted to 3-4 with 10N NaOH. Solids precipitated. These were filtered and dried, yielding 497 mg. The two batches of solids obtained above were combined and dissolved in ethanol. Approximately 1.1 e.g. of HCl in isopropanol (4.21M) was added, followed by ether to triturate the product as the HCl salt. The resultant solids were filtered and dried under high vacuum to yield 880 mg of a white solid: m.p. 98°–186° C. slow decomposition.

NMR (200 MHz,D$_6$DMSO) δ12.72(m,1H); 11.61(s,1H indole NH); 8.85(m,1H amide NH); 9.68(m,1H ammonium NH); 9.53(m,1H, ammonium NH); 7.70(m,1H); 7.45(m,2H); 7.3–6.98(m,8H); 6.55(d,1H,J=9 Hz); 5.91(d,1H,J=6 Hz); 5.36(s,2H); 4.48(d,2H,J=7 Hz); 4.24(m,1H); 4.13(m,2H);

3.53–2.98(m,3H); 2.57(t,2H,J=7 Hz); 1.54(t of t, 2H, J=7,7 Hz); 1.37–1.20(m,8H); 0.84(t,3H,J=7 Hz).

FAB MS: Calcd for $C_{37}H_{42}ClN_5O_5$: 672.30. Found: 672.36.

The following compounds can be prepared by the procedure described in Example 1, Part C:

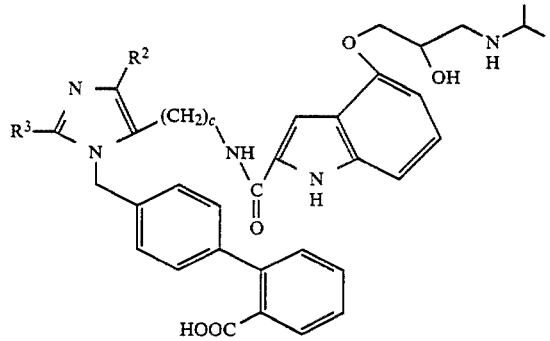

| Example No. | $R^2$ | $R^3$ | n | m.p. |
|---|---|---|---|---|
| 87 | Cl | n-butyl | 2 | |
| 88 | Cl | n-butyl | 3 | |
| 89 | Cl | n-butyl | 4 | |
| 90 | Cl | n-butyl | 5 | |
| 91 | Cl | n-propyl | 1 | |
| 92 | Cl | n-propyl | 2 | |
| 93 | Cl | n-propyl | 3 | |
| 94 | Cl | n-propyl | 4 | |
| 95 | Cl | n-propyl | 5 | |
| 96 | $CF_3$ | n-propyl | 1 | |
| 97 | Br | n-propyl | 1 | |
| 98 | I | n-propyl | 2 | |
| 99 | F | n-propyl | 2 | |
| 100 | $NO_2$ | n-propyl | 3 | |
| 101 | $CF_3$ | n-propyl | 4 | |
| 102 | Br | n-propyl | 4 | |
| 103 | F | n-propyl | 5 | |
| 104 | $NO_2$ | n-propyl | 5 | |
| 105 | $CF_3$ | n-butyl | 1 | |
| 106 | Br | n-butyl | 1 | |
| 107 | I | n-butyl | 2 | |
| 108 | F | n-butyl | 2 | |
| 109 | $NO_2$ | n-butyl | 3 | |
| 110 | $CF_3$ | n-butyl | 4 | |
| 111 | Br | n-butyl | 4 | |
| 112 | F | n-butyl | 5 | |
| 113 | $NO_2$ | n-butyl | 5 | |

Utility

A rationale for incorporating β-adrenoceptor blocking activity into ACE inhibitors is that ACE inhibition often evokes a secondary increase in renin, which may limit the inhibitory action of ACE inhibitors [Allan et al., Cardiovascular Drug Reviews, 6, 84–96 (1988)]. Since renin increase is sensitive to β-adrenoceptor blockade [MacGregor, et al., J. Cardiovascular Pharmacology, 7, 582–587 (1985)], molecules that possess both the β-adrenoceptor and ACE inhibiting activities may have a better therapeutic profile than an ACE inhibitor alone.

Since the saralasin-induced renin release in rats and humans is also sensitive to β-adrenoceptor blockade [Keeton, et al., Pharmacological Review, 31, 81–227, (1981)], a molecule with β-adrenoceptor blocking and angiotensin II (AII) receptor antagonistic activities should exhibit a similar improved therapeutic profile as described above. In this regard, AII antagonism combined with β-adrenoceptor blockade is superior to the combination of ACE inhibition and β-adrenoceptor blockade. ACE inhibitors do not totally block the formation of AII [Schmidt, et al., J. Cardiovasc. Pharmacol., 8(Supp. 10):S100–S105 (1986)], since other peptidyl dipeptidases may be responsible for the production of AII. In contrast, AII receptor antagonists will block the vasoconstrictive effect of AII because it will inhibit all of AII, irrespective of the source, at its own receptor. Furthermore, ACE inhibitors potentiate the bradykinin effect which leads to side effects in humans such as dry cough [Moore, et al., Lancet: 1116–1118 (1987)]. AII receptor antagonists do not potentiate the bradykinin effect which may obviate the side effects seen with ACE inhibitors.

In the pithed rat, compared to the vehicle-treated group (n=4) Example 1 at 3 (n=4) and 30 mg/kg i.v. (n=3) shifted the dose-pressor response curve for AII about 2 and 10 fold to the right, respectively (FIG. 1). In the same model, Example 1 at 3 (n=4) and 30 mg/kg i.v. (n=4) caused a rightward shift of the dose-tachycardiac response curve for isoproterenol (a β-adrenoceptor agonist) by 10 and 30 fold, respectively (FIG. 2). These results demonstrate that Example 1 is a molecule possessing AII antagonistic and β-adrenoceptor blocking activities.

Dosage Forms

The compounds of this invention can be administered for the treatment of hypertension according to the invention by any means that effects contact of the active ingredient compound with the site of action in the body of a warm-blooded animal. For example, administration can be parenteral, i.e., subcutaneous, intravenous, intramuscular, or intraperitoneal. Alternatively, or concurrently, in some cases administration can be by the oral route.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 0.5 to 500 milligrams per kilogram of body weight. Ordinarily, from 1 to 100, and preferably 2 to 80, milligrams per kilogram per day in one or more applications is effective to obtain desired results.

The active ingredient can be administered orally in solid dosage forms, such as capsules, tablets, and powders, or in liquid dosage forms, such as elixirs syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as substained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol. The solution is made to volume with water for injection and sterilized.

Suspension

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

We claim:

1. An antihypertensive compound of the formula:

(I)

$$-CQ^3OH-CQ^1Q^2-NQ-B$$

wherein $Q$ and $Q^1$-$Q^6$ are independently selected from hydrogen and alkyl of 1-4 carbon atoms;

$P$ is a carbonyl group or $$-\overset{O}{\underset{\|}{C}}-NH- \text{ or } -\overset{O}{\underset{\|}{C}}-O-$$

with N and O, respectively, bonded to Ar;

$B$ is an alkyl group of 1 to 6 carbon atoms;

Any of the $-(CH_2)_c-$ groups independently are optionally substituted by one or two alkyl groups of 1 to 4 carbon atoms;

Ar is a benzene ring or a naphthyl or indolyl ring system any of which is optionally substituted in any position by one or more substituents independently selected from alkyl groups of 1 to 4 carbon atoms being optionally substituted by one or more halogen atoms, alkosy of 1 to 9 carbon atoms, halogen, nitro, amino, carboxy, alkoxycarbonyl of 1 to 4 carbon atoms, and hydroxy;

$R^1$ is $-4-COOH$; $-4-CO_2R^7$;

$NHSO_2CF_3$; $CONHOR^9$.

$R^2$ is H, F, Cl, Br, I, $NO_2$, alkyl of one to six carbon atoms, perfluoroalkyl of one to six carbon atoms, phenyl, pentafluorophenyl, CN, $COR^{16}$;

$R^3$ is alkyl of 2 to 10 carbon atoms, alkenyl or alkynyl of 3 to 10 carbon atoms, alkylthio of 2-10 carbon atoms;

$R^4$ is H; Cl; Br; F; $NO_2$; alkyl of 1 to 4 carbon atoms; acyloxy of 1 to 4 carbon atoms; alkoxy of 1 to 4 carbon atoms; $CO_2H$; $CO_2R^7$; $NHSO_2CH_3$; $NHSO_2CF_3$; $CONHOR^9$; $SO_2NH_2$; phenyl or furyl;

$R^5$ is H; Cl, Br, I or F; alkyl of 1 to 4 carbon atoms or alkoxy of 1 to 4 carbon atoms;

$R^6$ is $$-CO_2H;\ -CO_2R^7;\ -CH_2CO_2H,\ -CH_2CO_2R^7;\ -O-\overset{O}{\underset{\underset{OH}{|}}{\overset{\|}{S}}}-OH;$$

-continued $-O-\overset{\overset{O}{\|}}{\underset{OH}{P}}-OH$; $-SO_3H$; $-NH\overset{\overset{O}{\|}}{\underset{OH}{P}}-OH$;

$-PO_3H$; $-C(CF_3)_2OH$; $-NHSO_2CH_3$; $-NHSO_2CF_3$; $-NHCOCF_3$; $-CONHOR^9$; $-SO_2NH_2$;

$-CH_2-\underset{\underset{H}{N}}{\overset{N-N}{\diagup\!\diagdown}}N$; $-CONH-\underset{\underset{H}{N}}{\overset{N-N}{\diagup\!\diagdown}}N$; $CONHNHSO_2CF_3$;

$\underset{\underset{H}{N}}{\overset{N-N}{\diagup\!\diagdown}}-CF_3$; $\underset{R^{15}}{\overset{N=N}{\diagup\!\diagdown}}-NH$; or $-\underset{\underset{H}{N}}{\overset{N}{\diagup}}\overset{N}{\underset{N}{\diagdown}}$;

$R^7$ is $-\overset{R^{14}}{\underset{|}{CH}}-O\overset{O}{\overset{\|}{C}}R^{11}$;

$R^8$ is H, alkyl of 1 to 6 carbon atoms, cycloalkyl of 3 to 6 carbon atoms, phenyl or benzyl;

$R^9$ is H, methyl or benzyl;

$R^{11}$ is alkyl of 1 to 6 carbon atoms; $-NR^{12}R^{13}$; or $-\underset{\underset{NH_2}{|}}{CH}CH_2CO_2CH_3$ $R^{12}$ and $R^{13}$ are independently H, alkyl of 1 to 6 carbon atoms, benzyl, or are taken together as $(CH_2)_u$ where u is 3 to 6;

$R^{14}$ is H, $CH_3$ or $-C_6H_5$;

$R^{15}=CN$, $NO_2$ or $CO_2R^8$;

$R^{16}$ is H; alkyl of 1 to 6 carbon atoms; phenyl; phenylalkyl where alkyl is 1 to 6 carbon atoms; OH; alkoxy of 1 to 6 carbon atoms; phenoxy; benzyloxy; $NH_2$; alkylamino or dialkylamino where alkyl is 1 to 6 carbon atoms; or morpholino;

X is a carbon-carbon single bond, $-CO-$, $-O-$, $-S-$, $-NH-$, $-NHCO-$, $-CONH-$, $-OCH_2$, $-CH_2O-$, $-CH=CH-$, $-SCH_2-$, $-NHCH_2-$, $-CH_2-$, $-CH_2S-$, $-CH_2NH-$;

Z=O, S;

c=1 to 10;

r=0 to 2; or a pharmaceutically acceptable salt of these compounds.

2. Compound of claim 1 which is 5-[4-(3-(N-isopropylamino)hydroxypropoxy)indole-2-carboxamidomethyl]-2-n-butyl-1-[(2'-carboxybiphenyl-4-yl)methyl]-4-chloroimidazole.

3. A pharmaceutical composition comprising a pharmaceutically suitable carrier and an effective amount of a compound of claim 1.

4. A method of treating hypertension in a warm-blooded animal comprising administering to the animal a compound of claim 1 in an amount effective to lower the animal's blood pressure.

5. A method of treating congestive heart failure in a warm-blooded animal comprising administering to the animal a compound of claim 1 in an amount effective to correct the hemodynamic burden on the heart to relieve the congestion.

* * * * *